United States Patent [19]

Berges et al.

[11] Patent Number: 5,670,500

[45] Date of Patent: Sep. 23, 1997

[54] WATER SOLUBLE CAMPTOTHECIN ANALOGS

[75] Inventors: David A. Berges, Provo, Utah; John J. Taggart, Elkins Park, Pa.

[73] Assignee: SmithKline Beecham Corporation, Philadephia, Pa.

[21] Appl. No.: 454,794

[22] Filed: May 31, 1995

[51] Int. Cl.$^6$ ............... A61K 31/47; C07D 491/147
[52] U.S. Cl. ............... 514/233.2; 514/253; 514/228.5; 514/279; 544/60; 544/125; 544/361; 546/41
[58] Field of Search ............ 544/125; 514/233.2

[56] References Cited

U.S. PATENT DOCUMENTS

| | | | |
|---|---|---|---|
| 4,939,255 | 7/1990 | Tagawa | 544/125 |
| 5,004,758 | 4/1991 | Boehm et al. | 514/283 |

FOREIGN PATENT DOCUMENTS 0 540 099 A1   5/1993   European Pat. Off. .

OTHER PUBLICATIONS

Wall, et al., "Plant Antitumor Agents. 30.[1a,b] Synthesis and Structure Activity of Novel Captothecin Analogs", (1993), *J. Med. Chem.*, 36:2689–2700.

Masuda et al., "CPT–11: A New Derivative of Camptothecin for the Treatment of Refractory or Relapsed Small–Cell Lung Cancer", (1992), *J. Clin. Oncology*, 10:1225–1229.

*Primary Examiner*—Donald G. Daus
*Attorney, Agent, or Firm*—Yuriy P. Stercho; Stephen A. Venetianer; Edward T. Lentz

[57] ABSTRACT

The present invention provides water soluble camptothecin analogs of Formula I:

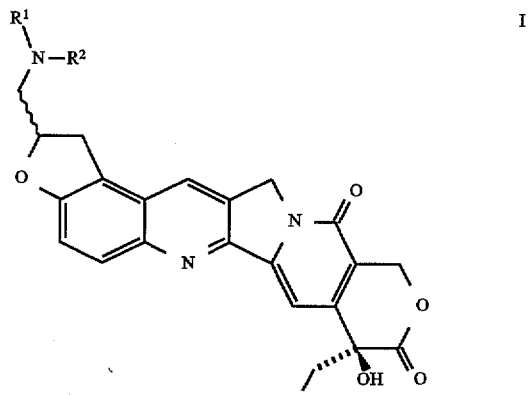

which are particularly useful as antineoplastic agents; pharmaceutical compositions thereof; and a method of treating cancer in an animal in need thereof, including human beings, comprising inhibition of the growth of tumor cells in said animal by administration of an effective amount of a compound of Formula I.

2 Claims, No Drawings

WATER SOLUBLE CAMPTOTHECIN ANALOGS

FIELD OF THE INVENTION

The present invention relates to water soluble camptothecin analogs which are particularly useful as antineoplastic agents, pharmaceutical compositions thereof, and methods of treatment of cancer in animals, including human beings, in need thereof comprising inhibition of the growth of tumor cells sensitive to such an analog.

BACKGROUND OF THE INVENTION

This invention relates to water soluble camptothecin analogs, a pharmaceutical composition comprising a tumor cell growth inhibiting amount of such an analog, and a method of inhibiting the growth of tumor cells sensitive to such an analog in an animal in need thereof.

The structure of the DNA helix within eukaryotic cells imposes certain topological problems that the cellular apparatus must solve in order to use its genetic material as a template. The separation of the DNA strands is fundamental to cellular processes such as DNA replication and transcription. Since eukaryotic DNA is organized into chromatin by chromosomal proteins, the ends are constrained and the strands cannot unwind without the aid of enzymes that alter topology. It has long been recognized that the advancement of the transcription or replication complex along the DNA helix would be facilitated by a swivel point which would relieve the torsional strain generated during these processes. Topoisomerases are enzymes that are capable of altering DNA topology in eukaryotic cells. They are critical for important cellular functions and cell proliferation.

There are two classes of topoisomerases in eukaryotic cells, type I and type II. Topoisomerase I is a monomeric enzyme of approximately 100,000 molecular weight. The enzyme binds to DNA and introduces a transient single strand break, unwinds the double helix (or allows it to unwind), and subsequently reseats the break before dissociating from the DNA strand.

Topoisomerase II consists of two identical subunits of molecular weight 170,000. Topoisomerase II transiently breaks both strands of the helix and passes another double-strand segment through the break.

Camptothecin is a water-insoluble, cytotoxic alkaloid produced by Camptotheca accuminata trees indigenous to China and Nothapodytes foetida trees indigenous to India. Camptothecin and a few close congeners thereof are the only class of compounds known to inhibit topoisomerase I.

Inhibition of topoisomerase II is the major target of important commercial oncolytic agents (e.g., etoposide, doxombicin and mitoxantrone) as well as other oncolytic agents still undergoing development. Camptothecin (and its known congeners) have no effect on topoisomerase II and none of the known topoisomerase II inhibitors has any significant effect on topoisomerase I.

Camptothecin and most of its analogs have not proven to be attractive for clinical drug development as cytolytic agents because of unacceptable dose limiting toxicity, unpredictable toxicity, poor aqueous solubility, unacceptable shelf life stability, and/or lack of clinical efficacy.

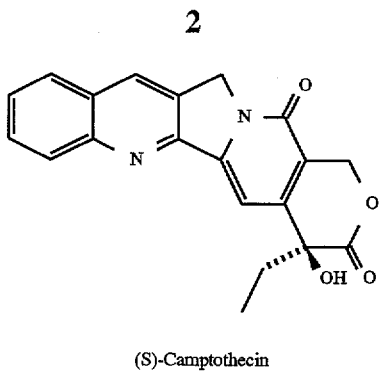

(S)-Camptothecin

Water soluble camptothecin analogs having efficacy as topoisomerase I inhibitor antineoplastic agents are known. U.S. Pat. No. 5,004,758, issued to Boehm, et al. on Apr. 2, 1991, the specification of which is incorporated herein by reference, discloses water soluble camptothecin analogs, preferably topotecan (9-dimethylaminomethyl-10-hydroxycamptothecin), preferably (S)-topotecan, of formula:

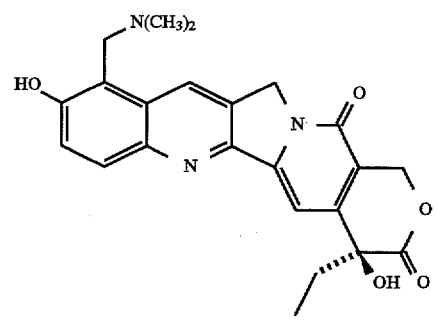

(S)-Topotecan most preferably as the hydrochloride salt. In clinical tests, topotecan has demonstrated efficacy against several solid tumor cancers, particularly ovarian cancer and non-small cell lung carcinoma in humans.

Masuda, et al., J. Clin, Oncology, 1992, 10, 1225–1229 describes CPT-11 ((S)-10-amino-4-ethyl-4-hydroxy-1H-pyrano[3',4':6,7]indolizino [1,2-b]quinoline-3,14(4H,12H)-dione). However, efforts to develop CPT-11 as an antineoplastic agent have been hampered by an adverse toxicity profile.

Wall, et al., J. Med. Chem,, 1993, 36, 2689–2700 describes 9-aminocamptothecin ((S)-[1,4'-bipiperidine]-1'-carboxylic acid, 4,11-diethyl-3,4, 12,14-tetrahydro-4-hydroxy-3,14-dioxo-1H-pyrano[3',4':6,7]indolizino [1,2-b] quinolin-9-yl ester). However, this compound possesses limited water solubility which has posed formulation and bioavailability problems in its development as an antineoplastic agent.

There is a need for new topoisomerase I inhibiting agents which avoid the undesirable features described above. The compounds of the present invention satisfy such need.

SUMMARY OF THE INVENTION

In a first aspect, the present invention provides compounds of Formula I:

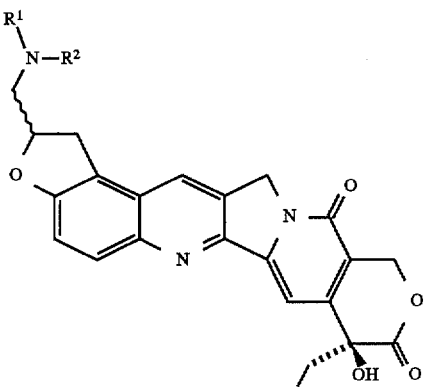

wherein:

R¹ and R² are H, $(C_{1-4})$alkyl or may together form a 5-to-7-membered heterocyclic ring containing the nitrogen and up to one additional heteroatom such as O, S, or $NR^3$ wherein $R^3$ is H or $(C_{1-4})$ alkyl, and pharmaceutically acceptable salts thereof.

In another aspect, the present invention relates to pharmaceutical compositions of compounds of Formula I.

In yet another aspect, the present invention relates to methods of treatment of cancer in animals, including human beings, in need thereof comprising inhibition of the growth of tumor cells by administration of an effective mount of a compound of Formula I, alone or in combination with a carrier, diluent or excipient.

DETAILED DESCRIPTION OF THE INVENTION

The terms below, defined as follows, are used in describing the present invention throughout this application.

"Aliphatic" is intended to include saturated and unsaturated groups. This includes normal and branched chains, saturated and mono- or polyunsaturated chains where double and triple bonds may be present in any combination.

The phrases "lower alkyl" and "$(C_{1-4})$ alkyl" refer to and mean an alkyl group of 1 to 4 carbon atoms in any isomeric form, but particularly the normal or linear form.

The term "5-to-7-membered heterocyclic ring containing the nitrogen and up to one additional heteroatom such as O, S, or $NR^3$" includes, but is not limited to, saturated rings such as piperidine, pyrrolidine, morpholine, thiomorpholine, piperazine, and N-alkylpiperazine.

The term "effective amount" means that amount of a compound or pharmaceutical composition of the present invention which, upon administration to an animal, including a human being, in need thereof for the treatment of cancer, provides a clinically desirable result in the treatment of such cancer as is understood by one of ordinary skill in the antineoplastic treatment art, including, but not limited to, inhibition of the growth of tumor cells, remission, or cure.

Salts may be made from these compounds, provided there is a sufficiently basic nitrogen present. Particularly preferred are the pharmaceutically acceptable salts of the instant compounds. These latter salts are those which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a manner well-known to those of ordinary skill in the art. The parent compound, dissolved in a suitable solvent, is reacted with an excess of an organic or inorganic acid. Representative acids are hydrochloric acid, hydrobromic acid, sulfuric acid, phosphoric acid, acetic acid, maleic acid, succinic acid or methanesulfonic acid.

Here and throughout this application, the ring system of the compounds of the present invention is numbered according to Formula II.

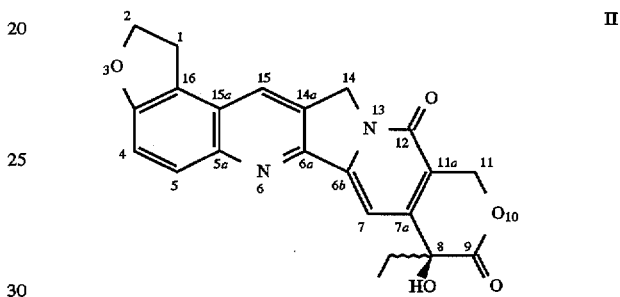

If a chiral center or another form of an isomeric center is present in a compound of the present invention, all forms of such isomer or isomers are intended to be covered herein. Inventive compounds containing a chiral center may be used as a racemic mixture, an enantiomerically enriched mixture, or the racemic mixture may be separated using well-known techniques and an individual enantiomer may be used alone.

The present invention provides compounds, and pharmaceutically acceptable salts thereof, which exhibit antineoplastic activity, said compounds having the structure represented by Formula I hereinabove.

No unacceptable toxicological effects are expected when compounds of the present invention are administered in accordance with the present invention.

The present invention provides a method of treatment of cancer in an animal, preferably a mammal, most preferably a human, in need of such treatment, comprising administering to such animal an effective amount of a compound of Formula I as described hereinabove, or a pharmaceutically acceptable salt thereof, alone or in combination with a carrier, excipient or diluent.

Preferred compounds of the present invention include the compound of Formula III, also known as (8S)-8-ethyl-1,2-dihydro-8-hydroxy-2(4-morpholinylmethyl)11H-furano[3,2-f]-pyrano[3',4':6,7]indolizino[1,2-b]quinoline-9,12(8H, 14H)-dione:

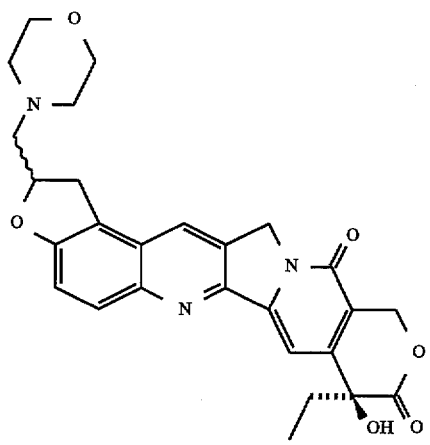

(8S)-8-Ethyl-1,2-dihydro-8-hydroxy-2-(4-morpholinylmethyl)-11H-furano[3,2-f]-pyrano[3',4':6,7]indolizino[1,2-b]quinoline-9,12(8H,14H)-dione and the compound of Formula IV, also known as (8S)-2-[(dimethylamino)methyl ]-8-ethyl-1,2-dihydro-8-hydroxy-11H-furano[3,2-f]-pyrano [3',4':6,7]indolizino[1,2-b]quinoline-9,12(8H,14H)-dione.

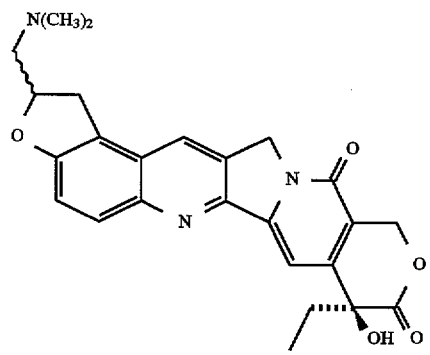

(8S)-2-[(Dimethylamino)methyl]-8-ethyl-1,2-dihydro-8-hydroxy-2-(4-morpholinylmethyl)-11H-furano[3,2-f]-pyrano[3',4':6,7]indolizino[1,2-b]quinoline-9,12(8H,14H)-dione The in vitro assays used to test the compounds of the present invention for antitumor activity are well-known. A generalized description of these assays follows.

CHO Microtiter Cytotoxicity Assay

Chinese Hamster ovary cells are grown in Alpha MEM Medium with L-glutamine and nucleosides and containing 10% fetal bovine serum and 100 units per mL penicillin-streptomycin in 75 cm² canted neck tissue culture flasks. They are harvested from these flasks using 0.5% trypsin. Microtiter plates (96-well, sterile, flat bottom) (Corning 25860) are seeded with $1.6 \times 10^3$ wild-type (AUX-B1) Chinese Hamster ovary cells per well or $2 \times 10^3$ multidrug resistant ($CH^RC5$) Chinese Hamster ovary cells per well. The plates are incubated at 37° C., 5% $CO_2$ overnight to allow the cells to attach. The outside wells of each plate are not used, due to evaporation during the incubation time. They are filled with medium and used as blanks. The next day, the medium is aspirated from the wells and 180 μL of fresh medium is added to each well. Compounds are diluted from stock solution in DMSO into fresh medium to a 10X concentration containing 2% DMSO. Twenty μL of this is then added to the 180 μL of fresh meduim in the wells. The plates are then incubated for another 3 days at 37° C., 5% $CO_2$. Eight mg of XTT (SIGMA X-4251) is dissolved in 100 μL of DMSO which is then added to 3.9 mL of phosphate buffered saline without cations (PBS). Phenazine methosulfate (SIGMA P-9625) is dissolved in PBS to a concentration of 3 mg/mL and 20 μL of this is added to the XTT solution. Fifty μL of this XTT/PMS solution is added to each well of the microliter plate and the plates are incubated for 90 minutes at 37° C., 5% $CO_2$ (until the $OD_{450}$~1.0). The plate is then read on a UV Max plate reader, using wells without cells .(i.e., containing only 200 μL of medium and 50 μL of XTT/PMS solution) as a background control.

Cleavable Complex Formation Assay (Topoisomerase I Inhibition)

Two μL of test compound is added to each well of a 96-well microliter plate. Ten μL of cleavage buffer (80 mM Tris HCl, 200 mM KCl, 20 mM $MgCl_2$, 1 mM EDTA pH8, and 1 mM DTT) is then added to each well. Four μL of pBR325 (200 ng) is then added to each well, followed by four μL of topoisomerase I (50 nM final concentration). The plate is incubated for 5–10 minutes at 37° C. Five μL of 5X stop buffer (2.5% SDS, 0.75 mg/mL Proteinase K (SIGMA P-0390) is then added to each well and the plate is incubated for 30 minutes at 37° C. Five μL of loading buffer (0.25% bromophenol blue, 0.25% xylene cyanol, 15% Ficoll 400) is added to each well and the entire contents of each well is then loaded on to a 1% agarose gel in TBE containing 0.5 μg/mL ethidium bromide. The gel is then run overnight at 25 volts and destained for one hour in 1 mM $MgSO_4$. DNA cleavage is quantified by imaging the gel and integrating the areas of the bands corresponding to open circular and supercoiled DNA.

The efficacy of the compounds of the present invention was also tested in vivo using three well-known mouse tumor models: L1210, Lewis Lung, and Colon Carcinoma 26.

Table I provides a comparison of the the topoisomerase I inhibition ability, cytotoxicity, and efficacy in mouse tumor models of the compounds of the present invention of Formulae III and IV with the known compounds topotecan and camptothecin. These results demonstrate that the compounds of Formulae III and IV have biological activity which is comparable to camptothecin and topotecan.

TABLE I

| Compound | Topoisomerase I Inhibition $CC_{50}$ (μM) | Cytotoxicity $IC_{50}$ (μM) | | Efficacy in Mouse Tumor Models % Inc. in Lifespan/Dose (mg/kg) | | |
|---|---|---|---|---|---|---|
| | | Wild Type (AUX-B1) | Multidrug Resistant | L1210 | Lewis Lung | Colon 26 |
| Topotecan | 0.55 | 0.79 | 2.3 | 217/15 ip | 106/15 ip | 45/20 sc |
| Camptothecin | 0.45 | 0.015 | 0.035 | 133/12 ip | | 50/4 ip |
| Formula III | 0.91 | 0.0055 | 0.42 | 350/42 ip | >225/22 ip | 45/20 sc |
| Formula IV | 0.6 | 0.018 | 1.0 | 225/15 ip | 67/9 ip | 32/20 sc |

Compounds of Formula I are prepared by the method described in Scheme 1. 10-Hydroxycamptothecin (1), available from camptothecin by the process described in U.S. Pat. No. 5,004,758, is allylated to give (2) using a base such as sodium hydride in dimethylformamide followed by addition of an allyl halide such as the bromide. Claisen rearrangement of 2 at elevated temperature in a high-boiling, unreactive solvent such as triglyme gives the allyl phenol 3. Treatment of 3 with an iodinating agent such as iodine monochloride in the presence of a halide-trapping agent such as silver nitrate gives iodo ether 4, which upon reaction with an amine gives the compounds of Formula I.

Scheme 1

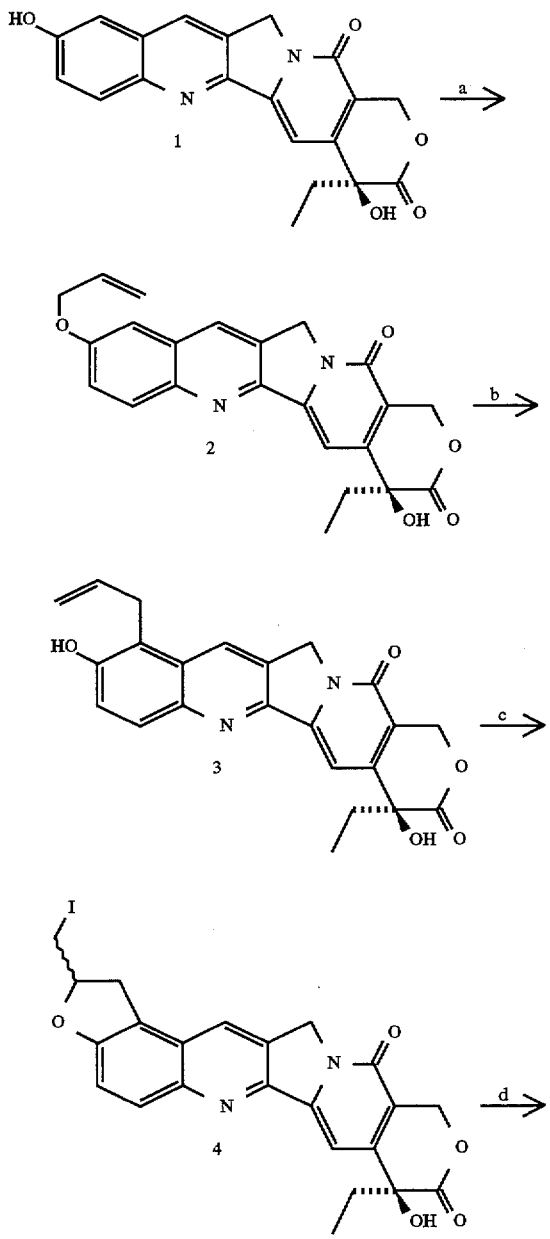

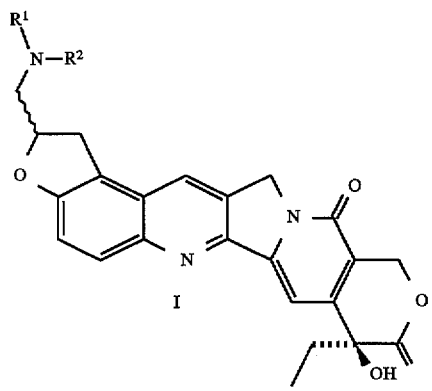

a) NaH, DMF, allyl bromide; b) Triglyme, 210° C.;
c) ICl, AgNO$_3$, CHCl$_3$, pyridine; d) HNR$^1$R$^2$, DMF The present invention provides pharmaceutical compositions prepared from the compounds of Formula I. These compositions have both a human and a veterinary utility, and comprise an excipient, diluent, or carrier which is acceptable for the intended pharmaceutical end use and at least one inventive compound. For example, if a veterinary use is intended, the carrier may be a liquid, or spray, or may be formulated in a solid, non-degradeable or degradeable form for insertion in the rumen. Selected excipients and carriers may be employed to prepare compositions acceptable or adaptable for human use.

An effective amount of one or more pharmaceutical compositions of the present invention may be contained in one embodiment, such as in a single pill, capsule, or pre-measured intravenous dose or pre-filled syringe for injection. Alternatively, as is frequently the case, the composition will be prepared in individual dose forms where one unit, such as a pill, will contain a sub-optimal dose but the user will be instructed to take two or more unit doses per treatment. When the composition is presented as a cream, it will contain a discrete amount of drug and the user will apply some amount of the cream one or more times until the disease is in remission or has been effectively treated. Concentrates for later dilution by the end user may also be prepared, for instance for intravenous (IV) formulations and multi-dose injectable formulations.

Excipients, diluents, or carriers contemplated for use in these compositions are generally known in the pharmaceutical formulary arts. Reference to useful materials can be found in well-known compilations such as *Remington's Pharmaceutical Sciences*, Mack Publishing Co., Easton, Pa.

The nature of the composition and the pharmaceutical excipient, diluent or carrier will, of course, depend upon the intended route of administration, for example whether by intravenous and intramuscular injection, parenterally, topically, orally, or by inhalation.

For parenteral administration the pharmaceutical composition will be in the form of a sterile injectable liquid such as an ampule or an aqueous or nonaqueous liquid suspension.

For topical administration the pharmaceutical composition will be in the form of a cream, ointment, liniment, lotion, paste, spray or drops suitable for administration to the skin, eye, ear, nose or genitalia.

For oral administration the pharmaceutical composition will be in the form of a tablet, capsule, powder, pellet, troche, lozenge, syrup, liquid, or emulsion.

The pharmaceutical excipient, diluent or carrier employed may be either a solid or liquid. When the pharmaceutical composition is employed in the form of a solution or suspension, examples of appropriate pharmaceutical carriers or diluents include: for aqueous systems, water; for non-aqueous systems: ethanol, glycerin, propylene glycol, olive oil, corn oil, cottonseed oil, peanut oil, sesame oil, liquid paraffins, and mixtures thereof with water; for solid systems: lactose, terra alba, sucrose, talc, gelatin, agar, pectin, acacia, magnesium stearate, stearic acid, kaolin and mannitol; and for aerosol systems: dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions. Similarly, the carrier or diluent may include time delay material well known to the art, such as glyceryl monostearate or glyceryl distearate alone or with a wax, ethylcellulose, hydroxypropylmethylcellulose, methylmethacrylate and the like.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. If a liquid carrier is used, the preparation will be in the form of a syrup, emulsion, soft gelatin capsule, sterile injectable solution or suspension in an ampule of vial or nonaqueous liquid suspension. To obtain a stable water soluble dose form, a pharmaceutically acceptable salt of the compound of Formula I is dissolved in an aqueous solution of an organic or inorganic acid or base. If a soluble salt form is not available, the compound of Formula I may be dissolved in a suitable co-solvent or combinations thereof. Examples of such suitable cosolvents include, but are not limited to, alcohol, propylene glycol, polyethylene glycol 300, polysorbate 80, glycerin and the like in concentrations ranging from 0–60% of the total volume.

It will be appreciated that the actual preferred dosages of the compounds used in the compositions and methods of treatment of the present invention will vary according to the particular complex being used, the particular composition formulated, the mode of administration and the particular site, host and tumor type being treated. Optimal dosages for a specific pathological condition in a particular patient may be ascertained by those of ordinary skill in the antineoplastic art using conventional dosage determination tests in view of the above experimental data. For parenteral administration, the dose of a compound of Formula I generally employed is from about 2 to about 50 mg/m$^2$ of body surface area per day for one to five days, preferably repeated about every fourth week for four courses of treatment. For continuous intravenous administration, the dose of a compound of Formula I generally employed is about 0.5 mg/m$_2$/day for 5 to 21 days. For oral administration, the dose generally employed is from about 20 to about 150 mg/m$^2$ of body surface area per day for one to five days, with courses of treatment repeated at appropriate intervals.

EXAMPLES

In the following synthetic examples, temperature is in degrees Centigrade (°C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

EXAMPLE 1

Preparation of (8S)-8-ethyl-1,2-dihydro-8-hydroxy-2-(4-morpholinylmethyl)-11H-furano [3,2-f]pyrano[3', 4':6,7] indolizino[1,2-b]quinoline-9,12(8H,14H)-dione dihydrochloride hydrate 1A. (S)-10-Allyloxycamptothecin Dry (S)-10-hydroxycamptothecin (10.0 g, 0.027 mol) was suspended with stirring in dry DMF (275 mL) at room temperature. Sodium hydride (80% suspension in mineral oil) (0.873 g, 0.0291 mol) was added in one portion; the mixture upon stirring for 0.33 h afforded an amber solution. Allyl bromide (3.96 g, 0.032 mol) was added; after stirring for 5 h a precipitate appeared; the olive green mixture was stirred overnight at ambient temperature. The reaction mixture was evaporated to dryness, and the residue was partitioned between water and chloroform and then filtered to remove some insoluble material. The aqueous phase was re-extracted with chloroform, and the combined organic extract was dried (sodium sulfate) and evaporated to a brown residue. This residue was dissolved in methanol containing some methylene chloride. The solvent was boiled off until incipient turbidity, and then upon cooling the solution gave a light brown solid in three crops (6.86 g, 63%). $^1$NMR (250 MHz, CDCl$_3$) δ 8.20 (s, 1H), 8.09 (d, J=9.4 Hz, 1H), 7.60 (s, 1H), 7.47 (dd, J=9 Hz and J=2 Hz, 1H), 7.13, (d, J=2.4 Hz, 1H), 6.20-6.00 (m, 1H), 5.69 (d, J=16.4 Hz, 1H), 5.48 (d, J=17.1 Hz, 1H), 5.40-5.20 (m, 3H), 5.68 (d, J=4.2 Hz, 2H), 3.80 (s, 1H), 2.00-1.80 (m, 2H), 1.02 (t, J=7.5 Hz, 3H).

1B. (S)-9-Allyl-10-hydroxycamptothecin (S)-10-Allyloxycamptothecin (3.0 g, 0.0074 mol) in triethyleneglycol dimethyl ether (20 mL) was heated in an oil bath at 210° C. for 0.33 h. After cooling to room temperature, hexane (200 mL) was added to the mixture, and a solid was collected, washed with hexane, and dried. The solid was taken up in methylene chloride containing a small amount of methanol and chromatographed on silica gel using a step gradient of 0–5% methanol in methylene chloride to afford the tire compound (1.04 g, 34%). $^1$H NMR(400 MHz, CDCl$_3$+CD$_3$OD) δ 8.37 (s,1H), 7.92 (d,J= 9.1 Hz, 1H), 7.63 (s,1H), 7.45 (d,J=9.2 Hz, 1H), 6.09-6.02 (m, 1H), 5.68 (d,J=16.2 Hz, 1H), 5.29 (d,J=16.2 Hz, 1H, 5.23 (d,J=19 Hz, 1H), 5.15 (d,J=19 Hz, 1H), 5.05 (d,J=9.9 Hz, 1H), 4.94 (d, J=18.8 Hz, 1H), 3.82 (d,J=5.4 Hz, 2H), 1.94-1.88 (m,2H), 1.03 (t,J=7.4 Hz, 3H). Anal.: ($C_{23}H_{20}N_2O_{30}\cdot\frac{3}{4}H_2O$) calcd.: C, 66.09; H, 5.19; N, 6.70 found : C, 66.06; H,5.10; N, 6.61.

1C. (8S)-8-ethyl-1,2-dihydro-8-hydroxy-2-iodomethyl-11H-furano [3,2f]pyrano[3',4':6,7]indolizino[1,2-b]quinoline-9,12(8H,14H)-dione Silver nitrate (6.8 g, 0.040 mol) in dry, freshly distilled chloroform (50 mL) and dry pyridine (20 mL) was treated, dropwise, with stirring with a solution of iodine monochloride (6.48 g, 0.0400 mol) in dry chloroform (40 mL) over a two min period. After stirring for 15 min, the mixture was centrifuged; the supernatent was then added to a solution of (S)-9-allyl-10-hydroxycamptothecin (3.92 g, 0.00960 mol) in dry chloroform (15 mL) giving a deep amber solution which was stirred overnight at ambient temperature. The solution was concentrated to a small volume and then partitioned between methylene chloride and water. After separation of the layers, the aqueous phase was re-extracted with methylene chloride. The combined organic layer was washed successsively with ice cold 5% aq. HCl, dilute sodium thiosulfate solution, and finally with water. The solution was dried (sodium sulfate) and evaporated to a golden-brown residue which was triturated with a small amount of cold methanol to afford the tire compound as a light brown solid. (2.25 g, 44%). $^1$H NMR (400 MHz, $CDCl_3$) δ 8.10 (d,J=4.3 Hz, 1H), 8.07 (d,J=9.2 Hz, 1H), 7.61 (s, 1H), 7.40 (dd,J=7.1 Hz and J=2.0 Hz, 1H), 5.73 (d,J=1.63 Hz, 1H), 5.29 (d,J=16.3 Hz, 1H), 5.26 (s, 2H), 5.20-5.10 (m, 1H), 3.83-3.81 (m, 1H), 3.72-3.70 (m, 1H), 3.57-3.54 (m, 1H), 3.49-3.46 (m, 1H), 3.39-3.38 (m, 1H), 1.92-1.84 (m, 2H), 1.03 (t,J=7.3 Hz, 3H). Anal.: ($C_{23}H_{19}IN_2O_5\cdot\frac{1}{2}H_2O$) calcd.: C, 51.22; H, 3.74; N, 5.19 found: C, 51.03; H, 3.56; N, 4.87.

1D. (8S)-8-ethyl-1,2-dihydro-8-hydroxy-2-(4-morpholinylmethyl)-11H-furano [3,2-f]pyrano[3',4':6,7]indolizino[1,2-b]quinoline-9,12(8H,14H)-dione dihydrochloride hydrate (8S)-8-Ethyl-1,2-dihydro-8-hydroxy-2-iodomethyl-11H-furano [3,2-f]pyrano[3',4':6,7]indolizino[1,2-b]quinoline-9,12(8H,14H)-dione (1.0 g, 0.0019 mol) in dry DMF (20 mL) was stirred with morpholine (0.78 g, 0.009 mol) at 45° C. for 6 h, and then overnight at ambient temperature. The solution was evaporated to dryness and taken up in methylene chloride. This solution was washed with water, and the organic layer was dried (sodium sulfate) and evaporated to a ruby syrup which was chromatographed on silica gel using a step gradient of 0–3% methanol in methylene chloride. Fractions containing the title compound as its free base were combined and evaporated to dryness. The residue was dissolved in water by adding 0.75 mL 2N HCl. The aqueous solution was lyophilized to yield the title compound as a fluffy solid (290 mg, 26%) $^1$H NMR (400 MHz, $CDCl_3$) δ 8.11 (s, 1H), 8.05 (d,J=8.9 Hz, 1H), 7.61 (s, 1H), 7.43 (d,J=9.1, 1H), 5.74 (d,J=16.4 Hz, 1H), 5.32-5.27 (m, 4H), 3.90-3.70 (m, 4H), 3.65-3.55 (m, 1H), 3.35-3.25 (m, 1H), 2.96-2.87 (m, 1H), 2.73-2.55 (m, 4H), 1.98-1.82 (m, 2H), 1.04 (t,J=7.4, 3H) Anal.: ($C_{27}H_{27}N_3O_6\cdot2HCl\cdot H_2O$) calcd.: C, 55.87; H, 5.38; N, 7.24 found: C, 55.69; H, 5.40; N, 7.13.

EXAMPLE 2

Preparation of (8S)-2-[(Dimethylamino)methyl]-8-ethyl-1,2-dihydro-8-hydroxy-11H-furano [3,2-f]pyrano[3',4':6,7]indolizino[1,2-b]quinoline-9,12(8H,14H)-dione dihydrotrifluoroacetate Into a stirred suspension of (8S)-8-ethyl-1,2-dihydro-8-hydroxy-2-iodomethyl-11H-furano [3,2-f]pyrano[3',4':6,7]indolizino[1,2-b]quinoline-9,12(8H,14H)-dione (0.830 g, 0.00156 mol), made according to the procedure set forth in Example 1C, in dry DMF (15 mL) at room temperature was bubbled gaseous dimethylamine to give a dark solution which was stirred overnight. The solution was evaporated to dryness in vacuo, and the residue was taken up in a mixture of methylene chloride and water. After separating layers, the aqueous phase was re-extracted with methylene chloride. The combined organic layer was washed with water, dried (sodium sulfate), and evaporated to a dark residue which was chromatographed on silica gel using a step gradient of 0–8% methanol in methylene chloride to afford free base of the title compound (150 mg). This material was taken up in water (200 mL) containing trifluoroacetic acid (0.1 mL). Lyophilization gave the title compound as a mustard-cream fluff (220 mg, 22%). $^1$H NMR(400 MHz, $CDCl_3+CD_3OD$) δ 8.14 (δ,J=17.8 Hz, 1H), 8.03-8.00 (m, 1H), 7.63 (d,J=3.6 Hz, 1H), 7.45-7.41 (m, 1H), 5.67 (d,J=16.2 Hz, 1H), 5.31-5.25 (m, 3H), 3.70-3.58 (m, 1H), 3.20-3.13 (m, 1H), 2.92-2.85 (m, 1H), 2.75-2.67 (m, 1H), 2.44 (d,J=2.9 Hz, 6H), 2.00-1.84 (m, 2H), 1.02 (t,J=7.4 Hz, 3H). Anal.: ($C_{25}H_{25}N_3O_5\cdot2C_2HF_3O_2$) calcd.: C, 50.22; H, 4.21; N, 6.06 found C, 50.50; H, 4.53; N, 6.16.

EXAMPLE 3

Parenteral Composition

To prepare a parenteral pharmaceutical composition of this invention suitable for administration by injection, 100 mg of a water soluble salt of a compound of Formula I is mixed with 10 ml of 0.9% sterile saline, and the mixture is incorporated into a dosage unit form suitable for administration by injection.

EXAMPLE 4

Oral Composition

To prepare an oral pharmaceutical composition of this invention, 100 mg of a compound of Formula I is mixed with 750 mg of lactose, and the mixture is incorporated into an oral dosage unit form, such as a hard gelatin capsule, which is suitable for oral administration.

Although the above specification and Examples fully describe the present invention, particularly the preferred embodiments thereof, it is understood that the present invention is not limited to these particular disclosed embodiments. Thus, the present invention includes all embodiments coming within the scope of the following claims.

We claim:
1. A compound of Formula III:

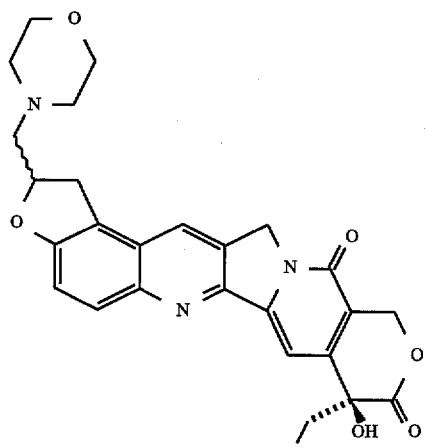

known as (8S)-8-ethyl-1,2-dihydro-8-hydroxy-2(4-morpholinylmethyl)-11H-furano [3,2-f]-pyrano [3',4':6,7] indolizino[1,2-b]quinoline-9,12(8H,14H)-dione.

2. A pharmaceutical composition comprising a compound of Formula III:

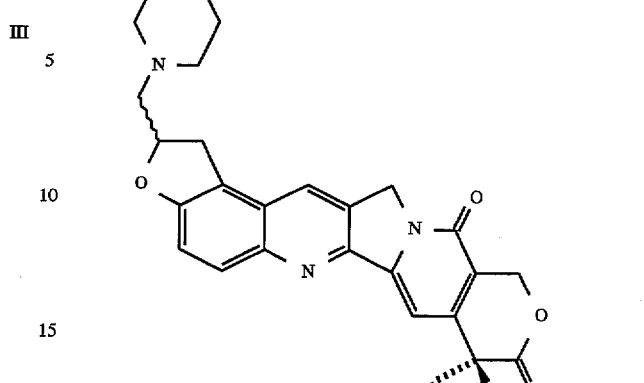

known as (8S)-8-ethyl-1,2-dihydro-8-hydroxy-2(4-morpholinylmethyl)-11H-furano [3,2-f]-pyrano [3',4':6,7] indolizino[1,2-b]quinoline-9,12(8H,14H)-dione, and pharmaceutically acceptable salts thereof, in combination with a carrier, diluent, or excipient.

* * * * *